United States Patent
Asher et al.

(10) Patent No.: US 7,237,431 B2
(45) Date of Patent: Jul. 3, 2007

(54) APPARATUS AND METHOD FOR MEASURING VISCOSITY

(75) Inventors: William E. Asher, Leominster, MA (US); Bradford J. Pope, Marlborough, MA (US); Zhou Zhou, Shrewsbury, MA (US)

(73) Assignee: On-Site Analysis, Inc., Marlborough, MA (US)

( * ) Notice: Subject to any disclaimer, the term of this patent is extended or adjusted under 35 U.S.C. 154(b) by 105 days.

(21) Appl. No.: 11/125,775

(22) Filed: May 10, 2005

(65) Prior Publication Data

US 2006/0254344 A1    Nov. 16, 2006

(51) Int. Cl.
  *G01N 11/06* (2006.01)
  *G01N 11/08* (2006.01)
  *G01N 11/00* (2006.01)
(52) U.S. Cl. .................. 73/54.07; 73/54.09; 73/54.16
(58) Field of Classification Search ............ 73/54.13, 73/54.19, 54.06, 54.09, 54.04, 54.07, 54.11, 73/54.14, 54.16, 54.17
  See application file for complete search history.

(56) References Cited

U.S. PATENT DOCUMENTS

| | | | | |
|---|---|---|---|---|
| 3,435,665 A | * | 4/1969 | Tzentis | 73/54.13 |
| 4,386,518 A | * | 6/1983 | Zatko | 73/54.09 |
| 4,539,837 A | * | 9/1985 | Barnaby | 73/54.06 |
| 4,615,210 A | | 10/1986 | Wright | |
| 4,680,958 A | * | 7/1987 | Ruelle et al. | 73/54.14 |
| 4,723,442 A | * | 2/1988 | Manning et al. | 73/54.07 |
| 4,750,351 A | | 6/1988 | Ball | |
| 4,890,482 A | * | 1/1990 | Maini | 73/54.14 |
| 4,916,678 A | | 4/1990 | Johnson et al. | |
| 5,257,529 A | | 11/1993 | Taniguchi et al. | |
| 5,365,776 A | * | 11/1994 | Lehmann et al. | 73/54.07 |
| 5,417,106 A | * | 5/1995 | Grudzien et al. | 73/54.14 |
| 6,681,616 B2 | * | 1/2004 | Spaid et al. | 73/54.07 |
| 6,691,561 B2 | * | 2/2004 | Lin et al. | 73/54.42 |
| 6,701,778 B2 | * | 3/2004 | Taylor | 73/64.48 |
| 6,732,574 B2 | | 5/2004 | Hajduk et al. | |
| 6,990,850 B2 | * | 1/2006 | Taylor | 73/54.06 |
| 7,040,144 B2 | * | 5/2006 | Spaid et al. | 73/54.05 |

* cited by examiner

*Primary Examiner*—Hezron Williams
*Assistant Examiner*—John Fitzgerald
(74) *Attorney, Agent, or Firm*—Thomas J. Engellenner; Michael P. Doyle; Nutter McClennen & Fish LLP

(57) ABSTRACT

An apparatus and methods for analysis of a petroleum product, specifically determining the viscosity of a sample, are disclose. The apparatus includes a sample reservoir for receiving a liquid sample and a pressure regulator for applying hyperbaric pressure to a sample within the reservoir. When pressure is applied to the sample reservoir, the sample is forced through a passageway and a pressure sensor monitors the pressure in the sample reservoir. A drop in the pressure can be used to determine when the reservoir is empty and sample viscosity can be calculated based on the time required to empty the reservoir.

43 Claims, 3 Drawing Sheets

APPARATUS AND METHOD FOR MEASURING VISCOSITY

BACKGROUND OF THE INVENTION

Proper viscosity is of critical importance for petroleum based oils to work effectively, whether the oils is used for lubrication, or otherwise. Under normal service, oil will degrade, adversely affecting its viscosity due to factors such as oxidation, nitration, and particulate contamination. Even under normal operating conditions, viscosity can degrade at a rapid pace. The result of viscosity degradation is often excessive motor wear and damage. As such, testing the viscosity of oil should be an essential part of any maintenance program.

Many types of viscometers are known in the art. One type is the capillary tube viscometer which consists of a capillary tube and a fluid reservoir that holds a specified volume of sample liquid. The force of gravity produces a hydrostatic head in the reservoir, which causes the liquid to flow through the capillary tube. The time required for a fixed fluid volume to flow through the capillary tube is measured and the viscosity of the fluid is calculated based on the recorded time and the dimensions of the viscometer. The capillary-tube viscometer thus allows a user to derive viscosity from Poiseuille's Law for the flow of fluids through a capillary tube.

However, used oil can be difficult to properly monitor. Typical oil borne contaminants such as wear metals, soot, particulates, glycol and water can cause a conventional viscometer to clog or jam. This can result in erroneous viscosity readings. In addition, thick, opaque motor oil is often not compatible with the optical sensors used to monitor the flow of a sample in conventional automated equipment. A residue of oil can cover such sensors and result in a false signal. Since an essential part of such a test is determining the time required to empty the fluid reservoir, conventional viscometers are problematic when measuring used oil samples.

Accordingly, a need exists for better viscometers that can provide more reliable viscosity data for viscous, and often contaminate-filled, samples.

SUMMARY OF THE INVENTION

The present invention provides apparatus and methods for evaluating the viscosity of a liquid sample. In one embodiment, the apparatus includes a sample reservoir for receiving a liquid sample and a pressure regulator for applying hyperbaric pressure to a sample within the reservoir. The sample reservoir includes an outlet passageway through which a sample can be forced when the sample reservoir is pressurized and a pressure sensor for monitoring the pressure in the sample reservoir.

In one aspect, the pressure regulator can comprise an accumulator. For example, air can be pumped into an accumulator to create a pressurized source of air. When needed, the pressurized air can be released from the accumulator. In another aspect, the pressure regulator can be a line or passageway for coupling the reservoir to a source of pressurized gas. The regulator also can include a restrictor positioned between a source of pressurized gas and the sample reservoir.

In one embodiment, the viscometer can include a processor in communication with the pressure sensor. The processor collects data from the pressure sensor and is adapted to sense an empty condition of the sample reservoir based on pressure readings. The processor can use those pressure readings to determine sample viscosity based on the length of time between a full condition and an empty condition.

In another embodiment, the viscometer can include multiple reservoirs. For example, the viscometer can include two reservoirs in parallel with one another. The reservoirs can be adapted for testing samples at different temperatures.

A method of measuring the viscosity of a sample is also disclosed herein. In one embodiment the method includes filling a sample reservoir with a sample and pressurizing the sample reservoir forcing the sample through a passageway. As the sample flows through the passageway, a senor senses pressure within the viscometer. The data collected from the sensor is used to determine when the sample reservoir is empty based on a change in pressure. Based on the time required to empty the sample reservoir, the viscosity of the sample is determined.

In another embodiment, the sensor is used to sense when the sample reservoir is full based on a change in pressure. Once the sample reservoir is full, pressure is applied to force the sample through the passageway.

In yet another aspect, the method includes the step of closing a valve positioned between a source of pressurized gas and the sample reservoir prior to, or during, the filling step. In addition, a valve disposed between the sample reservoir and a sample overflow line can be opened prior to, or during, the filling step.

Applying over-pressure to the sample reservoirs provides certain benefits over standard gravity-feed tube-type viscometers. A wider range of oils can be tested on a single device with over-pressure, without the need for adjustment or modification. High viscosity oils that will not flow through a capillary tube under the force of gravity can be forced through a similarly sized orifice or tube by applying over-pressure. By applying over-pressure, test-cycle time can also be reduced, making viscosity measurement more practical. Similarly, the over-pressure configuration of the invention, can greatly reduce or eliminate the clogging effects of contaminated (particle-laden) oils without reducing measurement accuracy.

The usage of a pressure sensor for detecting fluid flow also provides advantages over a similar system using optical sensors. In many cases, used oil contains contaminants making it, and any tubing it flows through, optically opaque. In such a case an optical sensor cannot detect sample presence once tubing walls have been coated.

BRIEF DESCRIPTION OF THE DRAWINGS

The invention can be more fully understood from the following detailed description taken in conjunction with the accompanying drawings, in which.

DETAILED DESCRIPTION OF THE INVENTION

The present invention provides methods and apparatus for the measurement of viscosity in a sample, preferably, a sample of a petroleum product. In one aspect, disclosed herein, is a viscometer having a sample reservoir for receiving a sample and a source of pressurized gas for creating an over-pressure condition in the sample reservoir. When a sample is delivered to the sample reservoir, the pressurized gas can be fed to the sample chamber to force a sample through a passageway, and thereby prevent clogging and/or move a thick sample through the viscometer.

To determine viscosity, the time required to empty the sample reservoir is calculated. Unlike conventional viscometers that use optical sensors, the viscometer disclosed herein senses changes in pressure to monitor sample flow. In one aspect, pressure data is used to determine the amount of time required to empty the sample reservoir of a sample. The length of time can then be used to calculate the viscosity of the liquid sample.

Figure 1:
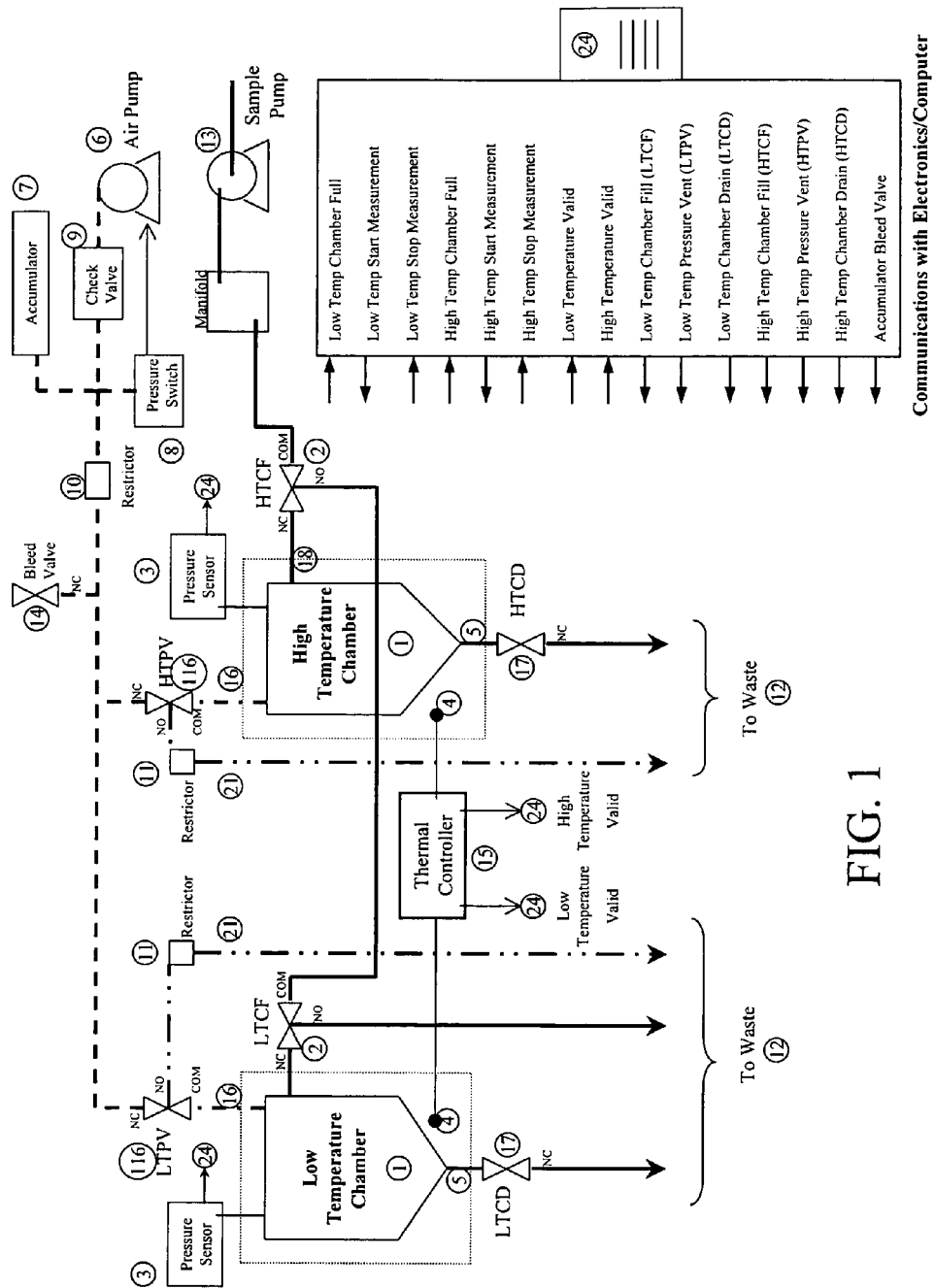
FIG. 1 is a schematic diagram of one embodiment of the viscometer device disclosed herein.
Figure 2:
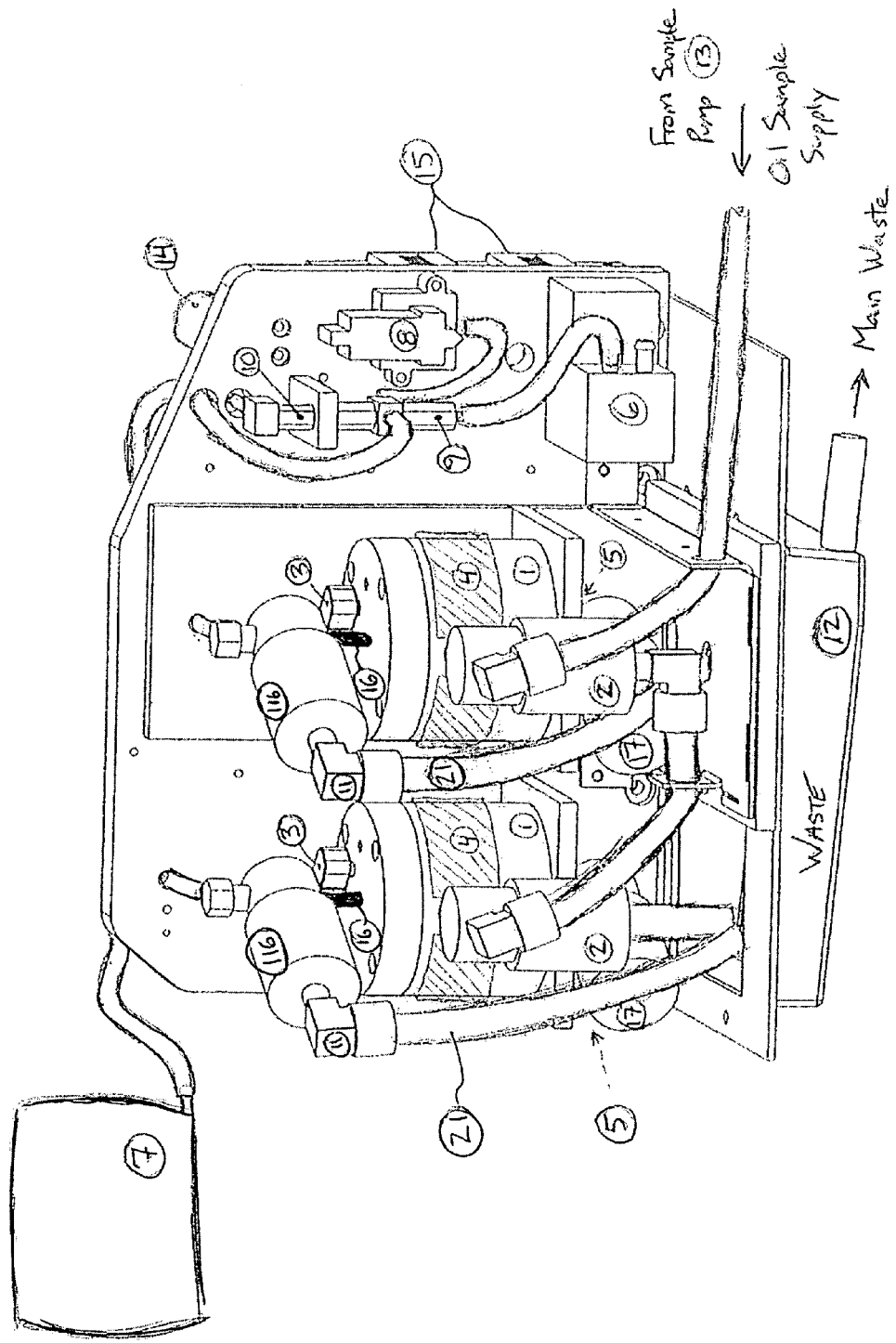
FIG. 2 is a perspective view of another embodiment of the viscometer disclosed herein.
Figure 3:
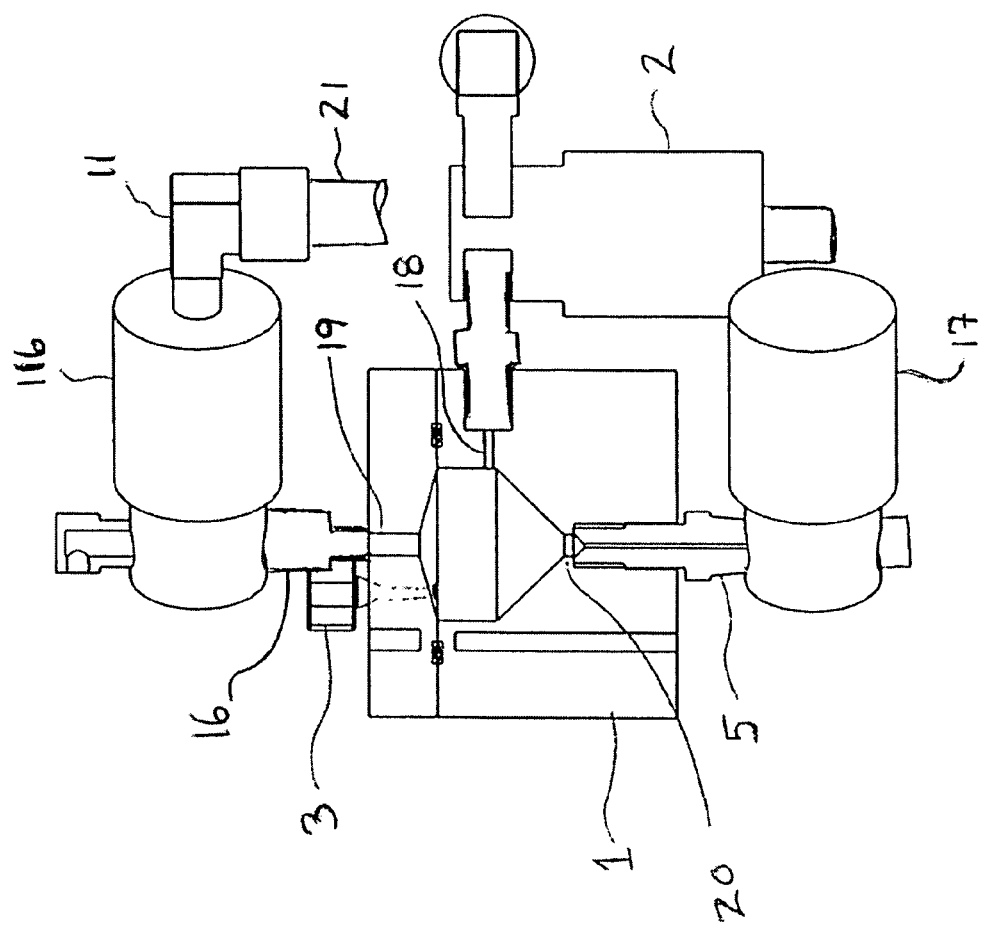
FIG. 3 is a cut-away view of a sampling reservoir in yet another embodiment of the viscometer disclosed herein.

FIG. 1 illustrates a schematic view of one embodiment of the viscometer 100 disclosed herein, including at least one sample reservoir 1 adapted to receive a liquid sample. Sample reservoir 1 can include a number of inlets and outlets for the ingress and egress of a sample and/or pressurized gas. In one aspect, sample reservoir 1 includes a sample inlet 18 for the delivery of a sample and a sample outlet passageway 5 for sample egress. Sample can be fed directly to sample reservoir 1, or by way of a sample pump 13, and can exit to a waste collector 12. Sample reservoir 1 can further include an outlet through which excess sample can be discharged to an overflow outlet 21 and an inlet through which a pressurized gas can be fed. In one aspect, line 16 provides a passageway for the delivery of pressurized gas and for the egress of excess sample. A three way valve 116 can control line 16. One skilled in the art will appreciate that while two sample reservoirs are illustrated in the FIGS. 1 and 2, the device could include a single sample reservoir (as shown in FIG. 3) or more than two sample reservoirs (e.g., three or more).

In some cases it is desirable to test a sample at two temperatures to investigate the relative change in viscosity of oil over a temperature range, effectively a measure of the amount of change of viscosity with respect to temperature. In one aspect, viscometer 100 includes two sample reservoirs positioned in parallel with one another. One of the samples reservoirs can be a "high" temperature sample reservoir and the other can be a "low" temperature sample reservoir. The terms "high" and "low" are relative to one another and can be chosen based on the standards used in viscosity calculations. For example, the low temperature sample reservoir can operate around 40° C. and the high temperature sample reservoir can operate at around 100° C. One skilled in the art will appreciate that the actual temperatures can vary, and a user may choose to evaluate a sample at a variety of temperatures.

To adjust the temperature of the sample within the sample reservoir, viscometer 100 can include a heater 4. In one aspect, the sample is heated indirectly while positioned within the sample reservoir(s) 1, by way of a heater attached to the sample reservoir. Alternatively, or additionally, a heater could be positioned within sample reservoir 1 and positioned in contact with the sample. A sample could also be pre-heated. For example, sample could be collected within a collection chamber and pre-heated prior to delivery to sample reservoir(s) 1.

In one embodiment of viscometer 100, the source of pressurized gas 7 is an accumulator. An air pump 6 can pump air from the surrounding environment into accumulator 7 to provide the source of pressurized gas. Alternatively, or in addition, the source of pressurized air could be an "off the shelf" bottle of pressurized air such as, for example, pressurized nitrogen. One skilled in the art will appreciate that a variety of pressurized gasses could be used. The pressurized gas can be regulated by a pressure regulator positioned between the source of pressurized air and the sample reservoir. The pressure regulator can alternatively include a variety of structures for adjusting pressure such as a passageway through which the pressurized gas passes, a valve, and/or a restrictor (discussed in more detail below). The term "hyperbaric" and "overpressure" as used herein are intended to mean pressure greater than the ambient pressure, e.g., greater than atmospheric pressure. In typical applications, the pressure applied to the sample can be within the range of about 0.5 psig and about 100 psig, more preferably from about 1 psig to about 30 psig.

Viscometer 100 also includes at least one pressure sensor 3. In one aspect, sensor 3 is positioned in sample reservoir 1 for detecting the pressure therein. In particular, sensor 3 can collect pressure data as sample reservoir 1 is being filled and/or as sample reservoir 1 is being emptied. The collected data can be used to determine the different states of viscometer 100, such as when the sample reservoir is full and when the sample reservoir is empty.

The sampling procedure beings with delivering to sample reservoir 1 via sample inlet 18. To avoid contamination with previous samples, a portion of the sample and/or a cleaning solution can first be pumped through the system and then the system can be purged with gas from accumulator 7. The sample outlet passageway 5 is then closed by valve 17 and sample reservoir(s) 1 is filled. Line 16 can be left open to allow displaced air within sample reservoir 1 to escape, while the inlet for pressurized gas is closed (e.g., three-way valve 116 is open between sample reservoir 1 and overflow outlet 21, and closed between sample reservoir 1 and the source of pressurized air). Preferably, the sample reservoir is completely filled with sample so that no air remains in the sample reservoir.

Pressure data can be used to determine when the sample reservoir is in a full condition. As the sample is then fed to reservoir 1, pressure data is collected by pressure sensor 3. The change in pressure within sample reservoir can be used to determine when sample reservoir has reached a full condition. As the sample fills the chamber and reaches the narrow dimensions of the overflow outlet, the pressure in the chamber will increase This increase can be used to signify a full condition.

To make the pressure change more pronounced a restrictor 11 can be placed between the exit of the overflow outlet and the sample reservoir. The restrictor is a small diameter opening or passageway that will cause a different pressure readings when the sample reservoir is filled to the point that the sample reaches the restrictor. Since gas generally has a low viscosity as compared with a liquid sample, the pressure required to force liquid (as compared to gas) through the restrictor is significantly higher. This difference in viscosity causes a jump in pressure when the liquid sample reaches the restrictor, and facilitates determination of a full condition in the sample reservoir. In one embodiment, the restrictor provides an opening having a diameter in the range of about 0.001 inches and 0.2 inches, preferably in the range of about 0.01 inches and 0.02 inches.

Pressure sensor 3, which is used to collect pressure data determining when the sample reservoir has reached a full condition, can be positioned in a variety of locations within viscometer 100. For example, sensor 3 can be positioned in the sample reservoir, between the sample reservoir and the restrictor, and/or between the pump and the sample reservoir.

Once sample reservoir 1 has reached a full condition the sample viscosity can be determined by measuring the time required to empty the sample reservoir. In one aspect, the sample inlet 18 is closed (by valve 2) and the sample overflow outlet 21 is closed. The inlet for pressurized gas to sample reservoir can be opened, and the source of pressurized gas can be turned on and delivered to sample reservoir 1. Once valve 17, which opens sample outlet passageway 5, is opened, time and pressure data can be collected.

Pressure data collected from the pressure sensor can be used to determine when the sample reservoir has been emptied of sample and thereby determine the amount of time required to force the sample through sample outlet passageway 5. When the sample has been expelled from sample reservoir 1, the pressure in the sample reservoir will drop. This pressure drop can be determined from the pressure data collected from the pressure sensor and used to recognize an empty condition in the sample reservoir. Based on the amount of time required to empty the sample reservoir, sample viscosity can be determined.

To increase the pressure signal detected by the pressure sensor, a second restrictor 10 can be positioned between the source of pressurized gas 7 and the sample reservoir 1. Restrictor 10 can be the point of smallest diameter in the line between the source of pressurized gas and the sample reservoir. When the sample has exited the sample reservoir, the pressure sensor will sense a drop is pressure, which will signal an empty condition in the sample reservoir.

The pressure sensor used to detect an empty condition in the sample reservoir can be the same sensor used to detect a full condition as described above. Alternatively, a second pressure sensor can be used for sensing an empty condition. For example, the second pressure sensor could be positioned in the sample reservoir, in the sample outlet passageway, and/or between the source of pressurized gas and the sample reservoir.

The sample outlet passage 5 through which the sample passes when exiting sample reservoir 1 can be an elongate tube. Preferably, sample passageway 5 is long enough to minimize turbulence such that the sample passes through the sample passageway with a generally laminar flow. The viscous resistance to the flow of the sample through the sample passageway allows viscometer 100 to calculate viscosity.

Viscometer 100 can further include a processor 24 for collecting data and/or controlling the viscometer. Pressure sensor(s) 3 can be in communication with processor 24 so that the processor can receive pressure data and use the pressure data to calculate viscosity. As described in more detail below, viscometer 100 can determine viscosity of a sample based only on pressure and time data.

Processor 24 can also control the valves, pressure sources, and/or heater within viscometer 100. For example, processor 24 can send signals to a valve at each of the inlets and outlets to the sample reservoir to control the flow of gas and liquid in and out of the sample reservoir. In addition, processor 24 can be in communication with heater 4 to heat the sample to a desired temperature and/or be in communication with a pressure source (e.g., a pressure switch 8) to control the delivery of pressurized gas to the sample reservoir.

In one embodiment, viscosity is calculated using viscometer 100 by comparing the time required to empty sample reservoir 100 of a sample with the time required to empty the sample reservoir of liquids of known viscosity. When the other variables, such as temperature, pressure, and viscometer dimensions are kept constant, the viscosity of the unknown sample can be determined by comparison. In one embodiment, a series of samples of known viscosity are tested in viscometer 100 and the time required to empty the sample reservoir of each sample is stored in the processor 24. Since the time required to force a sample through passageway 5 has a generally linear relationship to the sample's viscosity, the time required to empty sample reservoir 1 of a sample of unknown viscosity can be used to determine the sample's viscosity by correlation with the data from the known samples.

As mentioned above, it is preferable to keep the sampling conditions (i.e., variables affecting viscosity) constant for the known samples and the unknown samples. Processor 24 can assist with keeping sampling conditions constant and/or adjust the calculations for variations in those variables. For example, it is preferable to keep the pressure applied to the sample reservoir constant. However, if the applied pressure varies, the processor can use the data collected from the pressure sensor to adjust the viscosity calculations. Similarly, it is preferable to keep the sample volume constant. However, heating the sample can cause some variations in sample volume and sample reservoir pressure. Reservoir volume and pressure can be adjusted by allowing a fraction of the sample to exit the sample reservoir.

FIG. 3 illustrates another embodiment of viscometer 100 in which only one sample reservoir is used. A sample can be delivered to sample reservoir 1 by way of a sample inlet 18 until sample reaches overflow port 19. Valve 2 is closed and gas from the source of pressurized air is fed through restrictor 11 and line 16 into sample reservoir 1. Pressure sensor 3 then collects pressure data as the sample is expelled through drain hole 20 into passageway 5. If a user wishes to perform another test at a different temperature, a second test can be run.

To calculate viscosity data with viscometer 100, a series of known samples can be tested with the viscometer. The time required to force these known samples through the outlet sample passageway 5 is recorded for each sample along with the sample temperature. The collected data is the stored in processor 24. For example, processor 24 for can have a look-up table with a series of viscosities and the amount of time required to pass through the outlet passageway. When an unknown sample is tested in viscometer 100, the amount of time required to flow through the passageway is recorded, preferably by monitoring pressure changes in the viscometer. The processor can then use the elapsed time (from the collected pressure data) and the data in the look-up table to determine sample viscosity.

Alternatively, the data collected from the known samples could be used to construct a viscosity equation for viscometer 100. For example, a linear equation can be found based on the data from the known samples. This equation is based on the linear relationship between sample viscosity and the time required for the sample to flow through the outlet passageway. When an unknown sample is tested, the time required for the sample to pass through the outlet passageway can be used, along with the viscosity equation, to calculate sample viscosity.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An apparatus for the measurement of the viscosity of a sample, comprising:
   a sample reservoir for receiving a liquid sample;
   a pressure regulator for applying hyperbaric pressure to a sample within the reservoir;
   a passageway through which a sample can be forced when the sample reservoir is pressurized;
   a pressure sensor for monitoring the pressure in the sample reservoir, whereby a drop in pressure indicates emptying of the reservoir and viscosity can be measured based on the time required to empty the reservoir; and a processor in communication with the pressure sensor, the processor adapted to sense an empty condition of the sample reservoir based on pressure readings received from the pressure sensor and to determine sample viscosity based on the length of time between a full condition and an empty condition.

2. The apparatus of claim 1, further comprising a heater for heating a sample in the sample reservoir to a desired temperature for viscosity measurement.

3. The apparatus of claim 1, wherein the pressure regulator further comprises an accumulator.

4. The apparatus of claim 1, wherein the apparatus further comprises a restrictor positioned between a sample overflow outlet and the sample reservoir.

5. The apparatus of claim 1, further comprising a processor in communication with the pressure sensor, the processor adapted to sense a full condition of the sample reservoir based on pressure readings received from the pressure sensor.

6. The apparatus of claim 1, wherein the apparatus further comprises a temperature sensor.

7. The apparatus of claim 1, wherein the apparatus further comprises pressure switch.

8. The apparatus of claim 1, further comprising a second sample reservoir.

9. The apparatus of claim 1, wherein the processor receives pressure data in real-time and is adapted to correct measured viscosity based on the real-time pressure data.

10. The apparatus of claim 1, further including a sample of a petroleum product.

11. The apparatus of claim 1, further comprising a calibration sample having a known viscosity.

12. The apparatus of claim 1, wherein the pressure regulator further comprises a coupling line for coupling the reservoir to a source of pressurized gas.

13. The apparatus of claim 12, wherein the apparatus further comprises a restrictor positioned in the coupling line.

14. A method of measuring the viscosity of a sample, comprising:

filling a sample reservoir with a sample;

pressurizing the sample reservoir and forcing the sample through a passageway;

sensing when the sample reservoir is empty based on a change in pressure in the sample reservoir;

determining the viscosity of the sample based on the amount of time required to empty the sample reservoir.

15. The method of claim 14, further comprising the step of sensing when the reservoir is full based on a change in pressure.

16. The method of claim 14, wherein the step of pressurizing the sample reservoir occurs when the sample reservoir is in a full condition.

17. The method of claim 14, further comprising the step of heating the sample in the sample reservoir.

18. The method of claim 14, further comprising the step of maintaining a constant volume of the liquid sample volume in the sample reservoir.

19. The method of claim 14, further comprising the step of monitoring pressure in real-time and using collected pressure data to correct the measured viscosity.

20. The method of claim 14, further comprising the step of closing a valve between a source of pressurized gas and the sample reservoir prior to, or during, the filling step.

21. The method of claim 20, further comprising the step of opening a valve between the sample reservoir and a sample overflow line prior to, or during, the filling step.

22. The method of claim 21, wherein a restrictor is positioned in the sample overflow line.

23. An apparatus for the measurement of the viscosity of a sample, comprising:

a sample reservoir for receiving a liquid sample;

a pressure regulator for applying hyperbaric pressure to a sample within the reservoir;

a passageway through which a sample can be forced when the sample reservoir is pressurized;

a pressure sensor for monitoring the pressure in the sample reservoir, whereby a drop in pressure indicates emptying of the reservoir and viscosity can be measured based on the time required to empty the reservoir; and a restrictor positioned between a sample overflow outlet and the sample reservoir.

24. The apparatus of claim 23, wherein the pressure regulator further comprises a coupling line for coupling the reservoir to a source of pressurized gas.

25. The apparatus of claim 23, further comprising a processor in communication with the pressure sensor, the processor adapted to sense a full condition of the sample reservoir based on pressure readings received from the pressure sensor.

26. An apparatus for the measurement of the viscosity of a sample, comprising:

a sample reservoir for receiving a liquid sample;

a pressure regulator for applying hyperbaric pressure to a sample within the reservoir;

a passageway through which a sample can be forced when the sample reservoir is pressurized;

a pressure sensor for monitoring the pressure m the sample reservoir, whereby a drop in pressure indicates emptying of the reservoir and viscosity can be measured based on the time required to empty the reservoir; and a processor in communication with the pressure sensor, the processor adapted to sense a full condition of the sample reservoir based on pressure readings received from the pressure sensor.

27. The apparatus of claim 26, wherein the apparatus further comprises a restrictor positioned between a sample overflow outlet and the sample reservoir.

28. The apparatus of claim 26, wherein the pressure regulator further comprises a coupling line for coupling the reservoir to a source of pressurized gas.

29. The apparatus of claim 28, wherein the apparatus further comprises a restrictor positioned in the coupling line.

30. An apparatus for the measurement of the viscosity of a sample, comprising:

a sample reservoir for receiving a liquid sample;

a pressure regulator for applying hyperbaric pressure to a sample within the reservoir;

a passageway through which a sample can be forced when the sample reservoir is pressurized;

a pressure sensor for monitoring the pressure in the sample reservoir, whereby a drop in pressure indicates emptying of the reservoir and viscosity can be measured based on the time required to empty the reservoir; and a pressure switch.

31. The apparatus of claim 30, wherein the apparatus further comprises a restrictor positioned between a sample overflow outlet and the sample reservoir.

32. The apparatus of claim 30, further comprising a processor in communication with the pressure sensor, the processor adapted to sense a full condition of the sample reservoir based on pressure readings received from the pressure sensor.

33. The apparatus of claim 30, wherein the pressure regulator further comprises a coupling line for coupling the reservoir to a source of pressurized gas.

34. The apparatus of claim 33, wherein the apparatus further comprises a restrictor positioned in the coupling line.

35. An apparatus for the measurement of the viscosity of a sample, comprising:
- a first and second sample reservoir for receiving liquid samples;
- a pressure regulator for applying hyperbaric pressure to a sample within the reservoirs;
- a passageway through which a sample can be forced when the sample reservoirs are pressurized;
- a pressure sensor for monitoring the pressure in the sample reservoirs, whereby
- a drop in pressure indicates emptying of the reservoirs and viscosity can be measured based on the time required to empty the reservoirs.

36. The apparatus of claim 35, wherein the apparatus further comprises a restrictor positioned between a sample overflow outlet and the first sample reservoir.

37. The apparatus of claim 35, further comprising a processor in communication with the pressure sensor, the processor adapted to sense a full condition of the first sample reservoir based on pressure readings received from the pressure sensor.

38. The apparatus of claim 35, wherein the pressure regulator further comprises a coupling line for coupling the first reservoir to a source of pressurized gas.

39. The apparatus of claim 38, wherein the apparatus further comprises a restrictor positioned in the coupling line.

40. An apparatus for the measurement of the viscosity of a sample, comprising:
- a sample reservoir for receiving a liquid sample;
- a pressure regulator for applying hyperbaric pressure to a sample within the reservoir;
- a passageway through which a sample can be forced when the sample reservoir is pressurized;
- a pressure sensor for monitoring the pressure in the sample reservoir, whereby a drop in pressure indicates emptying of the reservoir and viscosity can be measured based on the time required to empty the reservoir; and
- a processor capable of receiving pressure data in real-time and adapted to correct measured viscosity based on the real-time pressure data.

41. The apparatus of claim 40, wherein the apparatus further comprises a restrictor positioned between a sample overflow outlet and the sample reservoir.

42. The apparatus of claim 40, wherein the pressure regulator further comprises a coupling line for coupling the reservoir to a source of pressurized gas.

43. The apparatus of claim 42, wherein the apparatus further comprises a restrictor positioned in the coupling line.

* * * * *